United States Patent [19]

Dubreux

[11] 4,299,775
[45] Nov. 10, 1981

[54] PROCESS FOR THE PREPARATION OF 3-CYANO-3,5,5-TRIMETHYLCYCLOHEXANONE

[75] Inventor: Bernard Dubreux, Francheville Le Bas, France

[73] Assignee: PCUK Produits Chimiques Ugine Kuhlmann, Courbevoie, France

[21] Appl. No.: 185,989

[22] Filed: Sep. 10, 1980

[30] Foreign Application Priority Data

Oct. 26, 1979 [FR] France .................... 79 26596

[51] Int. Cl.³ .............................. C07C 120/02
[52] U.S. Cl. ........................................ 260/464
[58] Field of Search ........................... 260/464

[56] References Cited

U.S. PATENT DOCUMENTS

| | | | |
|---|---|---|---|
| 3,974,199 | 8/1976 | Plonka et al. | 260/464 |
| 3,992,432 | 11/1976 | Napier et al. | 260/465.1 X |
| 3,996,259 | 12/1976 | Lee et al. | 260/465.1 X |
| 4,022,816 | 5/1977 | Woods et al. | 260/464 X |
| 4,079,075 | 3/1978 | Lee et al. | 260/465.1 X |
| 4,174,347 | 11/1979 | Austermuhle-Bertola | 260/464 X |

FOREIGN PATENT DOCUMENTS 1452374 10/1966 France .
1047920 10/1964 United Kingdom .

OTHER PUBLICATIONS

C.A., 65, 1966, 8793d, Scholven Chemie A.G.

Primary Examiner—Joseph Paul Brust
Attorney, Agent, or Firm—Pennie & Edmonds

[57] ABSTRACT

Process for the preparation of 3-cyano-3,5,5-trimethylcyclohexanone from isophorone and cyanides, characterized by the fact that an organic phase containing the isophorone and an aqueous phase containing the cyanide are brought into contact in the presence of a catalytic amount of a phase transfer agent, such as quaternary ammonium or phosphonium salts.

5 Claims, No Drawings

PROCESS FOR THE PREPARATION OF 3-CYANO-3,5,5-TRIMETHYLCYCLOHEXANONE

TECHNICAL FIELD

Process for the preparation of beta-cyanoketone, 3-cyano-3,5,5-trimethylcyclohexanone, from isophorone and cyanides, characterized by the use of a two-phase system, and a phase transfer agent used in a catalytic amount.

BACKGROUND OF THE INVENTION

The action of hydrocyanic acid and cyanides on alpha-beta unsaturated ketones has been described. However, with the use of cyanides the reaction is slow, the contact times are high, and low yields are obtained. With the use of hydrocyanic acid the yields are good but the procedure is difficult to put into practice. In effect, the reaction temperatures are high, which most often makes it necessary to work under pressure. Moreover, since the reaction requires a basic catalyst, extensive precautions must be taken to avoid the highly exothermal polymerization of hydrocyanic acid.

SUMMARY OF THE INVENTION

The applicant has now discovered that 3-cyano-3,5,5-trimethylcyclohexanone can be synthetized with good selectivities and under mild conditions from isophorone and cyanides. To put the process according to the invention into practice an aqueous phase containing the cyanide is juxtaposed to an organic phase containing the isophorone in the presence of a catalytic amount of a phase transfer agent. The following reaction is then formally carried out:

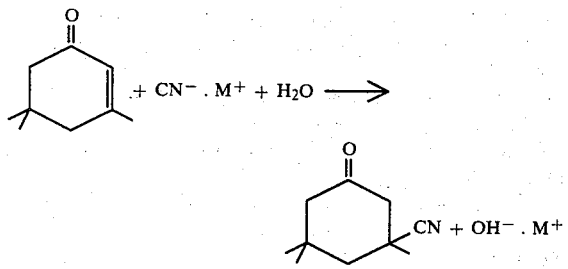

The organic phase which can be used according to the invention may be either a solution of isophorone in a solvent, or isophorone itself. The aqueous phase is obtained, e.g., by dissolving a cyanide in water or by neutralizing a base with hydrocyanic acid. After adding a catalytic amount of a transfer agent the two phases are brought together in a reactor provided with an efficient stirring means, and the system maintained at the desired temperature.

DETAILED DESCRIPTION OF THE INVENTION

The solvents which can be used according to the invention are selected solely as a function of the reaction temperature and the physical characteristics of 3-cyano-3,5,5-trimethylcyclohexanone, melting points, solubility, boiling points, etc., excluding all solvents which are miscible with water under the reaction conditions or which are capable of reacting with an aqueous cyanide solution. The solvents suitable for use include the hydrocarbons, ethers, esters, heavy alcohols, etc. The concentration of the isophorone in the organic phase may range between about 0.1% and saturation at the reaction temperature. A mixture of several solvents may be used.

The cyanides which may be used in the aqueous phase include all the cyanides soluble in water to an extent of more than about 0.1%. For example the cyanides of potassium or sodium can be used. The concentration of the cyanides in the aqueous phase may range between about 0.1% and saturation at the reaction temperature.

The molar ratio of isophorone to cyanide may vary within a broad range. This ratio will depend essentially on the ratio of the volumes of the aqueous phase and organic phase employed and on the respective solubilities of the cyanides and isophorone. This ratio usually ranges between about 0.01 and 10, and preferably between about 0.1 and 1.

The phase transfer agents which can be used according to the present invention are compounds which are soluble in the organic phase to an extent of more than about 0.01% and which, therefore, are chosen as a function of the nature of the organic phase employed. The molar ratio of catalyst to isophorone may range between about 0.00001 and 0.1 and preferably between about 0.0005 and 0.02.

Phase transfer agents, often referred to as phase transfer catalysts, are well known and described in the literature such as in British patent No. 1,540,632 published Feb. 14, 1976. Although many different phase transfer agents can be used according to the invention, the quaternary onium compounds are preferred. The quaternary ammonium and phosphonium salts are particularly advantageous in carrying out the reaction disclosed herein.

Examples of some specific transfer agents which may be advantageously used according to the present invention include the benzyltrimethylammonium, benzyltriethylammonium, tetramethylammonium, tetraethylammonium, tetrabutylammonium, dodecenyltriethylammonium, lauryldiethylbenzylammonium, etc. salts, and the tetraethylphosphonium, tetrabutylphosphonium, lauryltriethylphosphonium, lauryltributylphosphonium, tetraphenylphosphonium salts.

The reaction temperature usually ranges between about 0° C. and 100° C. and preferably between 60° C. and 90° C. The process may be carried out in a continuous or batchwise manner, preferably with agitation.

As the reaction proceeds the alkalinity of the aqueous phase increases as indicated by the above chemical equation. This increase in alkalinity may, if desired, be limited by the addition of buffering agents or by the progressive addition of an acid to the mixture. For example, hydrochloric acid, sulfuric acid or phosphoric acid can be used. Hydrocyanic acid, which has the advantage of regenerating the cyanide used up in the reaction, can also be used with advantage.

The following examples illustrate the present invention in a non-limitative manner:

EXAMPLE 1

An organic phase consisting of 0.360 mole of isophorone, and an aqueous phase consisting of a solution of 0.5 mole of sodium cyanide in 35 g of water, are brought into contact. After heating to 80° C., 1 g of lauryldimethylbenzylammonium bromide (LDMBAB) is introduced. After a reaction time of 4 hours at 80° C., with agitation, vapor-phase chromatographic analysis shows that 0.087 mole of 3-cyano-3,5,5-trimethylcyclohexanone has formed. The selectivity, expressed by the molar ratio of the cyanoketone formed to the isophorone converted is 90%. The 3-cyano-3,5,5-trimethylcyclohexanone is isolated from the reaction medium either by distillation at 146°–148° C. at 16 mm Hg or by crystallization.

EXAMPLE 2

In this example the organic phase consists of a solution of 0.360 mole of isophorone in 80 g of n-amyl alcohol, and the aqueous phase consists of a solution of 0.25 mole of sodium cyanide in 50 g of water. After heating to 70° C., 1 g of tetraethylammonium bromide is introduced and the reaction is allowed to proceed with agitation for 5 hours at 70° C. 0.057 mole of cyanoketone is obtained with a selectivity of 93%.

EXAMPLE 3

The process is carried out as in Example 2, except for using a solution of 0.1 mole of isophorone in 22 g of n-amyl alcohol and a solution of 0.7 mole of sodium cyanide in 70 g of water. 0.038 mole of cyanoketone is formed with a selectivity of 80%.

EXAMPLE 4

A solution of 0.05 mole of isophorone in 24 g of ligroin, and a solution of 1 mole of sodium cyanide and 0.05 mole of disodium phosphate in 100 g of water are brought in contact. After heating to 80° C. with agitation, 0.5 g of LDMBAB is introduced. The buffering agent maintains the pH of the aqueous solution in the vicinity of 12.5. After a reaction time of 2 hours at 80° C., with agitation, 0.022 mole of cyanoketone is formed with a selectivity of 81%.

EXAMPLE 5

The process is carried out according to Example 4, except for using 0.1 mole of isophorone dissolved in 24 g of ligroin, and 1 mole of sodium cyanide dissolved in 150 g of water. The buffer, consisting of 0.15 mole of disodium phosphate and 0.03 mole of soda, maintains the pH in the vicinity of 12.5. After a reaction time of 4 hours with agitation, 0.048 mole of cyanoketone is formed with a selectivity of 78%.

EXAMPLE 6

A solution of 0.2 mole of isophorone in 7 g of n-amyl alcohol is brought into contact with a solution of 1 mole of sodium cyanide in 100 g of water. After heating to 80° C., 1 g of LDMBAB is introduced, and then a 10% aqueous solution of hydrocyanic acid is poured in so as to maintain the pH in the vicinity of 11.5. After a reaction time of 3½ hours at 80° C., with agitation, 0.141 mole of cyanoketone is formed with a selectivity of 92%.

EXAMPLE 7

The process is carried out as in Example 6, except for using a solution of 0.5 mole of isophorone in a mixture of 100 g of ligroin and 14 g of n-amyl alcohol, and a solution of 2 moles of sodium cyanide in 200 g of water. The LDMBAB is added in an amount of 2 g, and the pH is adjusted to about 11.5 by pouring in a 30% aqueous solution of hydrocyanic acid. After a reaction time of 5 hours at 80° C. with agitation, 0.320 mole of cyanoketone is formed, with a selectivity of 98%.

I claim:
1. A process for the preparation of 3-cyano-3,5,5-trimethylcyclohexanone which comprises reacting isophorone alone or dissolved in a water immiscible organic solvent with a sodium or potassium cyanide dissolved in water in the presence of an onium phase transfer agent, at an alkaline pH, a temperature between about 0° and 100° C., and in which the isophorone-cyanide molar ratio is between about 0.01 and 10, and the transfer agent isophorone molar ratio is between about 0.00001 and 0.1.

2. The process according to claim 1 wherein the isophorone is dissolved in a solvent or a mixture of solvents to a concentration ranging between about 0.1% and saturation at the reaction temperature employed.

3. The process according to claim 1 wherein the cyanide ions are in the aqueous phase at a concentration ranging between about 0.1% and saturation at the reaction temperature.

4. The process according to claim 1, 2 or 3 in which the phase transfer agent is lauryldimethylbenzylammonium bromide or tetraethylammonium bromide.

5. The process according to claim 1 in which the temperature is between about 60° C. and 90° C., the isophorone-cyanide molar ratio is between about 0.1 and 1, and the transfer agent-isophorone molar ratio is between about 0.0005 and 0.02.

* * * * *